United States Patent [19]
Teuber et al.

[11] Patent Number: 5,902,813
[45] Date of Patent: May 11, 1999

[54] BENZIMIDAZOLE COMPOUNDS, PHARMACEUTICAL COMPOSITIONS CONTAINING THE COMPOUNDS AND THEIR USE

[75] Inventors: Lene Teuber, Vaerlose; Frank Wätjen, Herlev, both of Denmark

[73] Assignees: Neurosearch A/S, Glostrup, Denmark; Meiji Seika Kaisha, Ltd., Tokyo, Japan

[21] Appl. No.: 08/930,216

[22] PCT Filed: Apr. 19, 1996

[86] PCT No.: PCT/EP96/01654

§ 371 Date: Jan. 28, 1998

§ 102(e) Date: Jan. 28, 1998

[87] PCT Pub. No.: WO96/33192

PCT Pub. Date: Oct. 24, 1996

[30] Foreign Application Priority Data

Apr. 21, 1995 [DK] Denmark ................................ 0460/95

[51] Int. Cl.$^6$ ...................... A61K 31/505; C07D 239/42; C07D 403/10

[52] U.S. Cl. ..................... 514/275; 514/256; 514/339; 514/394; 544/331; 544/332; 544/333; 546/273.4; 548/306.1

[58] Field of Search ..................... 514/394, 256, 514/275, 339; 548/306.1; 546/273.4; 544/331, 333

[56] References Cited

FOREIGN PATENT DOCUMENTS

0616807A1  9/1994  European Pat. Off. .

*Primary Examiner*—Yogendra N. Gupta
*Attorney, Agent, or Firm*—Birch, Stewart, Kolasch & Birch, LLP

[57] ABSTRACT

The present patent application discloses compounds having the formula

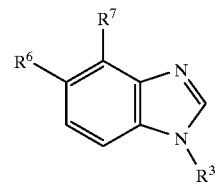

or a pharmaceutically acceptable salt thereof or an oxide thereof wherein $R_3$ is

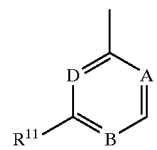

wherein A, B and D each is CH, or one or two of A, B and D is N and the others are CH;

$R^{11}$ is phenyl, benzimidazolyl, or monocyclic heteroaryl all of which may be substituted one or more times with substituents selected from alkyl, halogen, $CF_3$, amino, nitro, cyano, acylamino, alkoxy, acyl, phenyl, and monocyclic heteroaryl, and one of $R^6$ and $R^7$ is hydrogen and the other is pyrrolyl which may be substituted one or more times with substituents selected from halohen, alkyl, phenyl, and alkoxy.

The compounds are useful for the treatment of various central nervous system disorders such as epilepsy and other convulsive disorders, anxiety, sleep disorders and memory disorders.

8 Claims, 1 Drawing Sheet

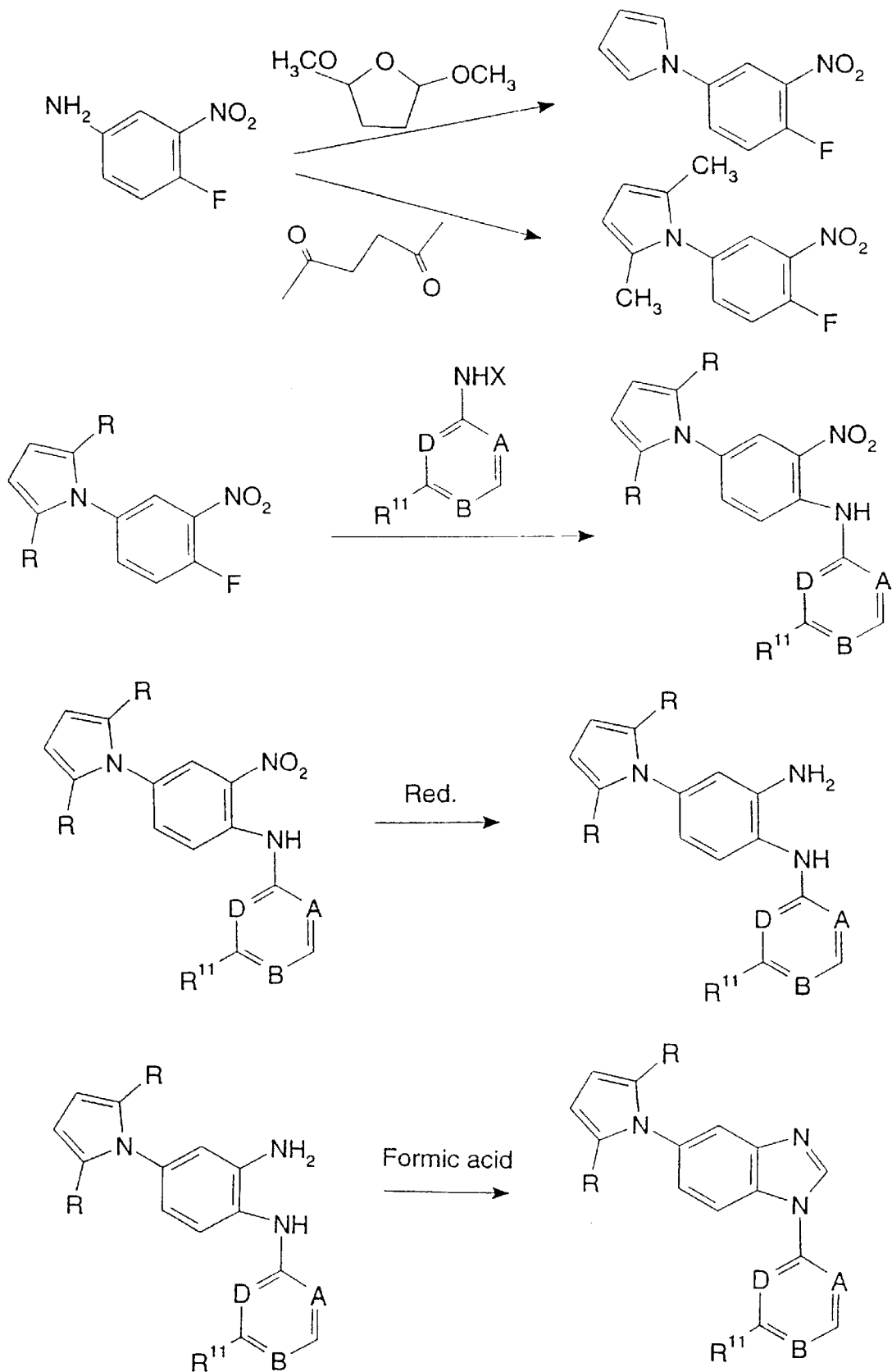

BENZIMIDAZOLE COMPOUNDS, PHARMACEUTICAL COMPOSITIONS CONTAINING THE COMPOUNDS AND THEIR USE

This invention relates to novel benzimidazole compounds, pharmaceutical compositions containing these compounds, methods of treating therewith, and to a method of preparing such benzimidazole compounds. The novel compounds are useful in the treatment of central nervous system diseases and disorders, which are responsive to modulation of the $GABA_A$ receptor complex, such as for example anxiety, sleep disorders, memory disorders, and epilepsia or other convulsive disorders.

BACKGROUND OF THE INVENTION

Receptors for γ-aminobutyric acid (GABA), $GABA_A$ receptors are the most abundant inhibitory receptors in mammalian brain. The $GABA_A$ receptor are structurally constituted as macromolecular heteropentameric assemblies (combinations of α, β, and γ/δ protein subunits). Several subtypes of such $GABA_A$ receptors have been described by techniques of modern molecular biology.

Each $GABA_A$ receptor complex comprises a chloride ion channel that controls chloride flux across the neuronal membrane, and multiple recognition sites for small modulatory molecules such as benzodiazepines, barbiturates, picrotoxin, and certain steroids. When GABA interacts with its receptor, the ion channel is opened, chloride influx is enhanced, the membrane is hyperpolarized and the cell becomes less responsive to excitatory stimuli. This GABA induced ion current can be regulated by diverse agents, including agents that interact with the benzodiazepine receptor or recognition site.

Agents that bind or interact with the modulatory sites on the $GABA_A$ receptor complex, such as for example the benzodiazepine receptor, can have either enhancing effect on the action of GABA, i.e. a positive modulatory effect of the receptor (agonists, partial agonists), an attenuating effect on the action of GABA, i.e. negative modulation of the receptor (inverse agonists, partial inverse agonists), or they can block the effect of both agonists and inverse agonists by competitive block (antagonists or ligands without intrinsic activity).

Agonists generally produce muscle relaxant, hypnotic, sedative, anxiolytic, and/or anticonvulsant effects, while inverse agonists produce proconvulsant, anti-inebriant, and anxiogenic effects. Partial agonists are characterized as compounds with anxiolytic effects but without or with reduced muscle relaxant, hypnotic and sedative effects, whereas partial inverse agonists are considered to be useful as cognition enhancers.

Numerous compounds belonging to different series of compounds having affinity for the benzodiazepine receptors have been synthesized during the last three decades. However, although the benzodiazepine receptor sites are still considered as very attractive biological sites for interfering with the CNS to treat various disorders and diseases, then nearly all previously synthesized compounds acting at these receptor sites have failed during clinical development because of unacceptable side effects.

The present invention provides novel benzimidazole compounds that interact with the benzodiazepine receptor of the $GABA_A$ receptor complex. The compounds of the present invention are valuable modulators of the $GABA_A$ receptor complex.

OBJECT OF THE INVENTION

It is an object of the present invention to provide novel benzimidazole compounds and pharmaceutically acceptable acid addition salts thereof, which are useful in the treatment of central nervous system disorders, diseases or ailments, which are responsive to the modulation of the $GABA_A$ receptor complex, especially positive modulation of the $GABA_A$ receptor complex.

Another object of the present invention is to provide pharmaceutical compositions comprising the novel benzimidazole compounds being useful for the above purposes. Still another object of the present invention is to provide a novel method of treating with the novel benzimidazole compounds.

A further object of the present invention is to provide a method of preparing the novel pharmaceutical compositions.

Additional objects will be obvious from the following description, and others will be obvious to one skilled in the art.

SUMMARY OF THE INVENTION

The invention then, inter alia, comprises the following, alone or in combination: A compound having the formula:

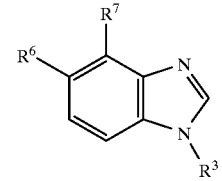

or a pharmaceutically acceptable salt thereof or an oxide thereof wherein $R^3$ is

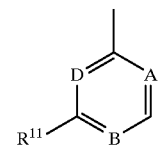

wherein

A, B and D each is CH, or one or two of A, B and D is N and the others are CH;

$R^{11}$ is phenyl, benzimidazolyl, or monocyclic heteroaryl all of which may be substituted one or more times with alkyl, halogen, $CF_3$, amino, nitro, cyano, acylamino, alkoxy, acyl, phenyl and monocyclic heteroaryl; and one of $R^6$ and $R^7$ is hydrogen and the other is pyrrolyl which may be substituted one or more times with substituents selected from halogen, alkyl, phenyl, and alkoxy;

a compound as above, which is 1-(3-(3-pyridyl)phenyl)-5-(1-pyrrolyl)benzimidazole, or 1-(3-(5-pyrimidinyl)phenyl)-5-(1-pyrrolyl)benzimidazole, or a pharmaceutically acceptable salt thereof or an oxide thereof;

a pharmaceutical composition comprising an effective amount of a compound as any above, or a pharmaceutically acceptable salt thereof or an oxide thereof, together with at least one pharmaceutically acceptable carrier or diluent;

the use of a compound as any above for the preparation of a medicament for the treatment of a disorder or disease of a living animal body, including a human, which disorder or disease is responsive to modulation of the GABA$_A$ receptor complex of the central nervous system;

the use of a compound as any above for the preparation of a medicament for the treatment of a disorder or disease of a living animal body, including a human, which disorder or disease is responsive to positive modulation of the GABA$_A$ receptor complex of the central nervous system;

the use of a compound as any above for the preparation of a medicament for the treatment of anxiety, sleep disorders, memory disorders, epilepsy or any other convulsive disorder;

a method of treating a disorder or disease of a living animal body, including a human, which disorder or disease is responsive to modulation of the GABA$_A$ receptor complex of the central nervous system, which comprises administering to such a living animal body, including a human, in need thereof a therapeutically-effective amount of a compound as any above;

a method as above, wherein a disorder or disease responsive to positive modulation of the GABA$_A$ receptor complex is treated;

a method as above, wherein anxiety, sleep disorders, memory disorders, epilepsy or any other convulsive disorder is treated; and the method as above, wherein the active ingredient is administered in form of a pharmaceutical composition thereof, in which it is present together with a pharmaceutically-acceptable carrier or diluent.

Halogen is fluorine, chlorine, bromine, or iodine.

Alkyl means a straight chain or branched chain of from one to eight carbon atoms or cyclic alkyl of from three to seven carbon atoms, including but not limited to, methyl, ethyl, propyl, isopropyl, butyl, isobutyl, t-butyl, pentyl, hexyl, cyclopropyl, cyclobutyl, cyclopentyl, cyclohexyl; methyl, ethyl, propyl, isopropyl and t-butyl are preferred groups.

Alkoxy means —O-alkyl, wherein alkyl is as defined above.

Acyl means —(C=O)-H or -(C=O)-alkyl, wherein alkyl is as defined above.

Acylamino is acyl-NH— wherein acyl is as defined above.

Amino is —NH$_2$ or —NH-alkyl or —N-(alkyl)$_2$, wherein alkyl is as defined above.

Monocyclic heteroaryl is a 5- or 6-membered heterocyclic monocyclic group. Such a monocyclic heteroaryl group includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 1 -imidazolyl, 2-imidazolyl, 4-imidazolyl, 1 -pyrrolyl, 2-pyrrolyl, 3-pyrrolyl, 2-furanyl, 3-furanyl, 2-thienyl, 3-thienyl, 2-pyridyl, 3- pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, and 4-pyrazolyl.

Examples of pharmaceutically-acceptable salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate for example.

Other acids such as oxalic acid, while not in themselves pharmaceutically acceptable may be useful in the preparation of salts useful as intermediates in obtaining compounds of the invention and their pharmaceutically acceptable acid addition salts. Such salts are formed by procedures well known in the art.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention exist in (+) and (−) forms as well as in racemic forms. Racemic forms can be resolved into the optical antipodes by known methods, for example, by separation of diastereomeric salts thereof, with an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallization of d- or I- (tartrates, mandelates, or camphorsulphonate) salts for example. The compounds of the instant invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolvation of optical isomers, known to those skilled in the art may be used, and will be apparent to the average skilled in the art. Such methods include those discussed by J. Jaques, A. Collet, and S. Wilen in "Enantiomers, Racemates, and Resolutions", John Wiley and Sons, New York (1981).

The compounds of the invention may be prepared in numerous ways. The compounds of the invention and their pharmaceutically acceptable derivatives may thus be prepared by any method known in the art for the preparation of compounds of analogous structure, and as shown in the representative examples which follows.

FIG. 1 describe methods for the preparation of compounds of the invention wherein $R^6$ is pyrrolyl and $R^7$ is hydrogen. Compounds of the invention wherein $R^7$ is pyrrolyl and $R_6$ is hydrogen can be synthesized analogously.

Starting materials for the processes described in the present patent application are known or can be prepared by known processes from commercially available chemicals.

The products of the reactions described herein are isolated by conventional means such as extraction, crystallization, distillation, chromatography, and the like.

Biology 4-aminobytyric acid (GABA) is the major inhibitory neurotransmitter and has been shown to act throughout both the central and peripheral nervous system. At present two types of GABA receptors are known, the GABA$_A$ and the GABA$_B$ receptors. Recent molecular biology has demonstrated that the GABA$_A$ receptors can be subdivided into numerous subreceptors consistent with the selective and or partial pharmacological effects observed with certain benzodiazepine receptor ligands as opposed to the unselective effects observed for the classical benzodiazepine receptor ligands such as for example diazepam. Activation of GABA receptors leads to alternations in membrane potential (hyperpolarization). The $GABA_A$ receptors are associated with chloride influx through its associated and integrated chloride channel, whereas $GABA_B$ receptor activation indirectly alters potassium and calcium channels as well as modifies second messenger production. The $GABA_A$ recognition sites can be activated by GABA, muscimol; and isoguvacine for example, but not by $GABA_B$ agonists such as for example baclofen. The modulatory $GABA_A$ recognition site at the benzodiazepine receptor sites can be selectively radiolabelled with $^3$H-flunitrazepam. The affinity of various potential ligands for the benzodiazepine receptor sites can thus be evaluated by estimating the ability of test compounds to displace $^3$H-flunitrazepam.

Method

Tissue Preparation:

Preparations are performed at 0–4° C. unless otherwise indicated. Cerebral cortex from male Wistar rats (150–200 g) is homogenized for 5–10 sec in 20 ml Tris-HCl (30 mM, pH 7.4) using an Ultra-Turrax homogenizer. The suspension is centrifuged at 27,000 ×g for 15 min and the pellet is washed three times with buffer (centrifuged at 27,000 ×g for 10 min). The washed pellet is homogenized in 20 ml of buffer and incubated on a water bath (37° C.) for 30 min to remove endogenous GABA and then centrifuged for 10 min at 27,000 ×g. The pellet is then homogenized in buffer and centrifuged for 10 min at 27,000 ×g. The final pellet is resuspended in 30 ml buffer and the preparation is frozen and stored at −20° C.

Assay:

The membrane preparation is thawed and centrifuged at 2° C. for 10 min at 27,000 ×g. The pellet is washed twice with 20 ml 50 mM Tris-citrate, pH 7.1 using an Ultra-Turrax homogenizer and centrifuged for 10 min at 27,000 ×g. The final pellet is resuspended in 50 mM Tris-citrate, pH 7.1 (500 ml buffer per g of original tissue), and then used for binding assays. Aliquots of 0.5 ml tissue are added to 25 μl of test solution and 25 μl of $^3$H-FNM (1 nM, final concentration), mixed and incubated for 40 min at 2° C. Non-specific binding is determined using clonazepam (1 μM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

The test value is calculated as the $IC_{50}$ (the concentration (nM) of the test substance which inhibits the specific binding of $^3$H-FNM by 50%).

Test results obtained by testing a selected compound of the present invention appear from the following table:

TABLE

| Test compound: | $IC_{50}$ (nM) |
|---|---|
| 1-(3-(3-pyridyl)-phenyl)-5-(1-pyrrolyl)-benzimidazole | 8.4 |

Pharmaceutical Compositions

While it is possible that, for use in therapy, a compound of the invention may be administered as the raw chemical, then it is preferable to present the active ingredient as a pharmaceutical formulation.

The invention thus further provides a pharmaceutical formulation comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, sub- cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing one (1) milligram of active ingredient or, more broadly, 0.01 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting vax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting vax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water propylene glycol solutions. For example, parenteral injection liquid preparations can be formulated in solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inner base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of this invention are extremely useful in the treatment of disorders or diseases of a living animal body due to their affinity for the benzodiazepine binding site of the $GABA_A$ receptor. These properties make the compounds of this invention extremely useful in the treatment of convulsions, anxiety, sleep disorders, memory disorders as well as other disorders sensitive to modulation of the $GABA_A$ receptor. The compounds of this invention may accordingly be administered to a subject, including a human, in need of treatment, alleviation, or elimination of a disorder or disease associated with the $GABA_A$ receptors. This includes especially convulsions, anxiety, sleep disorders and memory disorders.

Suitable dosage range are 0.01–100 milligrams daily, 0.1–50 milligrams daily, and especially 0.1–30 milligrams daily, dependent as usual upon the exact mode of administration, form in which administered, the indication towards which the administration is directed, the subject involved and the body weight of the subject involved, and further the preference and experience of the physician or veterinarian in charge.

The following examples will illustrate the invention further; however they are not to be construed as limiting.

EXAMPLE 1

2-Nitro-4-(1-pyrrolyl)fluorobenzene (1a): To a suspension of 4-fluoro-3-nitroaniline (20g, 0.13mol) in toluene (200mi) is added 2,5-dimethoxytetrahydrofuran (33ml, 0.26mol) and a catalytic amount of pTSA. The mixture is refluxed for 2.5 hours. After cooling the solvent is removed by evaporation and the residue is purified by column chromatography on silica gel using a mixture of ethyl acetate and petroleum ether (1:1) as the eluent. Yield: 23.1g (87%). Mp 79–81° C.

2-Nitro-4-(2,5-dimethylpyrrol- 1-yl)fluorobenzene (1 b): Prepared analogously from 4-fluoro- 3-nitroaniline and 2,5-hexanedione. Yield: 98%. Mp 99–101° C.

EXAMPLE 2

3-(3-Pyridyl)aniline (2a): A mixture of diethyl 3-pyridylborane (16.3g, 0.11 mol), 3-bromoaniline (12.2ml, 0.11mol), potassium carbonate (45.8g, 0.33mol) and tetrakis(triphenylphosphine)palladium(0) (80mg) in a mixture of water (40ml) and dimethoxyethane (80ml) is heated to 80° C. under a stream of nitrogen over night. After cooling the mixture is diluted with water and ethyl acetate and filtered through a fluted filterpaper. The layers are separated. The aqueous layer is extracted once with ethyl acetate. The combined organic phases are dried over sodium sulfate and concentrated under reduced pressure. The residue is dissolved in ethanol. Water is added and the mixture is evaporated to dryness. This residue crystallizes upon trituration with ice-cold water. The crystals are collected, dried and washed with petroleum ether to afford pure 2a (16.3g, 87%). Mp 75–76° C.

EXAMPLE 3

3-(5-Pyrimidyl)aniline (2b): A suspension of 5-bromopyrimidine (15g, 94.3mmol), 3-aminophenylboronic acid hemisulfate (19.3g, 104mmol), sodium bicarbonate (39.6g, 472mmol) and tetrakis(triphenylphosphine)palladium(0) (1 g) in a mixture of water (75ml) and dimethoxyethane (150ml) is heated to 80° C. under a stream of nitrogen over night. After cooling the mixture is poured into ice-water. The precipitate is filtered off, washed with water and dried to yield 2b (15g, 93%). Mp 164–165° C.

N-Acetyl 3-(5-pyrimidyl)aniline (2c): 2b is acetylated with acetic anhydride to afford 2c (15.4g, 82%). Mp 157–158° C.

EXAMPLE 4

3-(1-midazolyl)aniline (2d): A mixture of 1 -iodo-3-nitrobenzene (90g, 0.36mol), imidazole (54g, 0.79mol), potassium carbonate (54g, 0.39mol) and finely divided copper powder (1 g) is heated to 200° C. The melt is stirred for 2 hours under nitrogen. During the reaction water vapor is trapped by molecular sieves, placed between the reaction vessel and the condenser. Following the reaction the mixture is cooled to 100° C. and water is added. The mixture is allowed to cool to room temperature and the crude product is filtered off and dried. Recrystallization from toluene (200–250ml) affords pure 3-(1-imidazolyl)nitrobenzene (54.2g, 79%). Mp 101–102° C.

To 3-(1-imidazolyl)nitrobenzene (51.6g, 0.27mol) in acetic acid (500ml) is added palladium catalyst (5g 5% Pd on activated carbon) and the mixture is hydrogenated under pressure ($P_{start}$: 4bar) until the hydrogen uptake has ceased. The mixture is filtered through celite and the filtrate is evaporated to dryness to leave 2d as a lightbrown oil. Yield: 40.4g (93%).

N-Acetyl 3-(1-imidazolyl)aniline (2e): 2d (5.88g, 37mmol) is stir acetic anhydride (30m l) at ambient temperature for 1 hour. The mixture is poured into ice-water and rendered alkaline by addition of aqueous sodium hydroxide (12M). The product is filtered off, washed with water and dried to yield 2e (6.34g, 85%). Mp 181–183° C.

EXAMPLE 5

3-(2-Pyridyl)aniline (2f): To a solution of 2-(3-nitrophenyl)pyridine (prepared as described in *J. Chem. Soc.* 1958 p. 1759) (12.7g, 63.5mmol) in abs. ethanol is added palladium catalyst (1.3g 5% Pd on activated carbon) and the mixture is hydrogenated at ambient pressure until the hydrogen uptake has ceased. The mixture is filtered through celite and the filtrate is concentrated under reduced pressure. The residue is purified by column-chromatography on silica gel using a mixture of ethyl acetate and petroleum ether (9:1)as the eluent to afford 2f (9.5g, 88%) as a light brown oil.

N-Acetyl 3-(2-pyridyl)aniline (2g): A mixture of 2f (5.6g, 32.9mmol) and acetic anhydride (20ml) is stirred at ambient temperature for 1 hour. The mixture is poured into ice-water and rendered alkaline with 10M sodium hydroxide. The product is filtered off, washed with water and dried. Yield:

5.5g (79%). Mp 133–134° C.

EXAMPLE 6

2-(Dimethylamino)pyrimidine: A solution of 2-chloropyrimidine (5g, 43.65mmol) in dry THF (50ml) is saturated with gaseous dimethylamine. The mixture is stirred at ambient temperature for 1 hour followed by evaporation of solvent. The residue is partitioned between water and ethyl acetate. The aqueous phase is extracted with ethyl acetate. The combined organic phases are dried over sodium sulfate and evaporated to leave the product as a brownish oil. Yield 5.07g (94%).

5-Bromo-2-(dimethylamino)pyrimidine. The above product (5.07g, 41.22mmol) is dissolved in glacial acetic acid (25ml) and bromine (2.15ml, 41.95mmol) is added. The mixture is stirred for 30 min. at ambient temperature and then poured into ice-water. The mixture is rendered alkaline by addition of 10M sodium hydroxide. The product is filtered off, washed with water and dried to yield 4.72g (57%). Mp 162–164° C.

3-(2-(Dimethylamino)-5-pyrimidyl)aniline (2h): A mixture of 5-bromo-2-(dimethylamino)pyrimidine (6.76g, 33.17mmol), 3-aminophenylboronic acid hemisultat (7.4g, 39.78mmol) potassium carbonate (13.73g, 99.49mmol), 1,3-propanediol (12ml, 166mmol) and tetrakis(triphenylphosphine)palladium(0) (0.2g) in a mixture of water (30ml) and dimethoxyethane (60ml) is heated to 80° C. under nitrogen overnight. After cooling the mixture is diluted with water and ethyl acetate and is filtered through a fluted filterpaper. The layers are separated and the aqeous phase is extracted once with ethyl acetate. The combined organic phases are dried over sodium sulfate and evaporated to dryness. The residue is triturated with a mixture of ethyl acetate and petroleum ether (1:1) to leave crystalline 2h (5.26g, 74%). Mp 115.5–117° C.

N-Acetyl 3-(2-(dimethylamino)-5-pyrimidyl)aniline (2i): 2h is acetylated as described for 2g in Example 5 to yield 2i. Mp 183–188° C.

EXAMPLE 7

N-(3-(3-Pyridyl)phenyl)-2-nitro-4-(1-pyrrolyl)aniline (3a): A mixture of 1a (0.5g, 2.4mmol) and 2a (0.41g, 2.4mmol) in N-methyl-2-pyrrolidone (2.5ml) is heated to 120–135° C. for 2 days. After cooling water and diluted sodium hydroxide is added and the mixture is extracted with ethyl acetate. The extract is dried over sodium sulfate, and the solvent is evaporated to leave crude 3a. This crude product is purified by column-chromatography on silica gel using dichloromethane and subsequently a mixture of dichloromethane and methanol (9:1) as the eluents to yield pure 3a (0.61g, 71%) as an oil.

EXAMPLE 8

N-(3-(5-Pyrimidyl)phenyl)-2-nitro-4-(1-pyrrolyl)aniline (3b); To a stirred suspension of 2c (4.55g, 21.36mmol) in dry DMF (40ml) is added sodium hydride (0.85g of a 60% dispersion in mineral oil) at 0° C. under nitrogen. When the evolution of hydrogen has ceased 1a (4g, 19.42mmol) is added and the resulting mixture is stirred at 40° C. under nitrogen over night. After cooling the mixture is poured into water (200ml) and extracted with ethyl acetate. The combined extracts are dried over sodium sulfate, concentrated under reduced pressure and chromatographied on silica gel using ethyl acetate as the eluent. This procedure affords the acetylated product (2.8g) which is stirred in a mixture of dimethoxyethane (40ml) and 1 M aqeous sodium hydroxide (21 ml) at ambient temperature over night. The resulting mixture is diluted with water. The product is filtered off, washed with water and dried to yield 3b (2.4g, 35%). Mp 82–84° C.

N-(3-(1-midazolyl)phenyl)-2-nitro-4-(1-pyrrolyl)aniline (3c) was prepared analogously from 1a and 2e. Yield: 28%. Mp 129–130° C.

N-(3-(11-midazolyl)phenyl)-2-nitro-4-(2,5-dimethylpyrrol-1-yl)aniline (3d) was prepared analogously from 1b and 2e. Yield: 35%. Mp 191–194° C.

N-(3-(2-Pyridyl)phenyl)-2-nitro-4-(1-pyrrolyl)aniline (3e) was prepared analogously from 1a and 2g. Yield: 30%. The product was isolated as an oil.

N-(3-(2-(Dimethylamino)pyrimid-5-yl)phenyl)-2-nitro-4-(1-pyrrolyl)aniline (3f) was prepared analogously from 1a and 2i. Yield: 20%. Mp 166–168° C.

EXAMPLE 9

N-(3-(3-Pyridyl)phenyl)-2-amino-4-(1-pyrrolyl)aniline (4a): 3a (6g, 16.85mmol) is dissolved in a mixture of ethanol (100ml) and THF (25ml). Sodium sulfide nonahydrate (13.35g, 55.62mmol) and ammonium chloride (3g, 55.62mmol) is added and the mixture is heated to retlux for 1 hour. After cooling the mixture is poured into water (400ml) and the product is filtered off, washed with water and dried. Yield: 5.1g (93%). Mp 178–179° C.

N-(3-(5-Pyrimidyl)phenyl)-2-amino-4-(1-pyrrolyl)aniline (4b) was prepared analogously from 3b. Yield: 89%. Mp 190–192° C.

N-(3-(1-Imidazolyl)phenyl)-2-amino-4-(1-pyrrolyl)aniline (4c) was prepared analogously from 3c. Yield: 83%. Mp 207–212° C.

N-(3-(11-midazolyl)phenyl)-2-amino-4-(2,5-dimethylpyrrol-1-yl)aniline (4d) was prepared analogously in quantitative yield from 3d. Mp 190° C. (decomp.).

N-(3-(2-Pyridyl)phenyl)-2-amino-4-(1-pyrrolyl)aniline (4e) was prepared analogously from 3e. Yield: 98%. Mp 135–140° C.

EXAMPLE 10

N-(3-(2-(Dimethylamino)pyrimid-5-yl)phenyl)-2-amino-4-(1-pyrrolyl)aniline (4f): To a suspension of 3f (0.2g, 0.5mmol) in abs. ethanol is added palladium catalyst (5% Pd on activated carbon) and the mixture is hydrogenated at ambient pressure until the hydrogen uptake has ceased. The mixture is filtered through celite and the filtrate is concentrated under reduced pressure. This crude product is used directly for the next step. See Example 11.

EXAMPLE 11

1-(3-(3-Pyridyl)phenyl)-5-(1-pyrrolyl)benzimidazole (5a): A solution of 4a (5g, 15.34mmol) in formic acid (50ml) is heated to reflux for 45 min. After cooling the mixture is poured into a vigorously stirred mixture of crushed ice (100g) and aqueous sodium hydroxide (100ml, 12M). The precipitate is filtered off, washed with water and dried. This crude product is dissolved in a mixture of dichloromethane and ethyl acetate and filtered through a short silica gel column. The filtrate is evaporated to dryness and the residue is recrystallized from toluene. Yield: 3.5g (68%). Mp 176–177° C.

1-(3-(11-midazolyl)phenyl)-5-(1-pyrrolyl)benzimidazole (5c) was prepared analogously from 4c. Yield: 70%. Mp 131–134° C.

1-(3-(2-Pyridyl)phenyl)-5-(1-pyrrolyl)benzimidazole (5e) was prepared analogously from 4e. Yield: 49%. Mp 147–148° C.

1-(3-(2-(Dimethylamino)pyrimid-5-yl)phenyl)-5-(1-pyrrolyl)benzimidazole (5f) was prepared analogously from 4f. Yield: 32%. Mp 237–238° C.

EXAMPLE 12

1-(3-(5-Pyrimidyl)phenyl)-5-(1-pyrrolyl)benzimidazole (5b): A mixture of 4b (1.6g, 4.9mmol), dimethylformamide dimethylacetal (1 ml, 7.35mmol) and a catalytic amount of pTSA in dry toluene (15ml) is heated to reflux for 3 hours. The mixture is concentrated under reduced pressure and the residue is chromatografied on silica gel using successively ethyl acetate and a mixture of ethyl acetate and methanol (9:1) as the eluents. Yield of 5b: 1 .5g (91%). Mp 197–198° C.

1-(3-(1-Imidazolyl)phenyl)-5-(2,5-dimethylpyrrol- 1-yl) benzimidazole (5d) was prepared analogously from 4d. Yield: 23%. Mp 141–142° C.

We claim:
1. A compound having the formula:

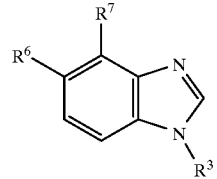

or a pharmaceutically acceptable salt thereof or an oxide thereof wherein $R^3$ is

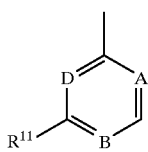

wherein

A, B and D each is CH, $R^{11}$ is phenyl, benzimidazolyl, or monocyclic heteroaryl all of which may be substituted one or more times with alkyl, halogen, $CF_3$, amino, nitro, cyano, acylamino, alkoxy, acyl, phenyl and monocyclic heteroaryl; and one of $R^6$ and $R^7$ is hydrogen and the other is pyrrolyl which may be substituted one or more times with substituents selected from halogen, alkyl, phenyl, and alkoxy.

2. A compound of claim 1, which is 1-(3-(3-pyridyl)phenyl)-5-(1-pyrrolyl)benzimidazole; or 1-(3-(5-pyrimidinyl)phenyl)-5-(1-pyrrolyl)benzimidazole;

or a pharmaceutically acceptable salt thereof or an oxide thereof.

3. A compound of claim 1, which is 1-(3-(1-Imidazolyl)phenyl)-5-(1-pyrrolyl)benzimidazole;

1-(3-(2-Pyridyl)phenyl)-5-(1-pyrrolyl)benzimidazole;

1-(3-(2-(Dimethylamino)pyrimid-5-yl)phenyl)-5-(1-pyrrolyl)benzimidazole; or 1-(3-(1-Imidazolyl)phenyl)-5-(2,5-dimethylpyrrol-1-yl)benzimidazole;

or a pharmaceutically acceptable salt thereof or an oxide thereof.

4. A pharmaceutical composition comprising an effective amount of a compound of any of claims 1–3, or a pharmaceutically-acceptable salt thereof or an oxide thereof, together with at least one pharmaceutically-acceptable carrier or diluent.

5. A method of treating a disorder or disease of a living animal body, including a human, which disorder or disease is responsive to modulation of the $GABA_A$ receptor complex of the central nervous system, which comprises administering to such a living animal body, including a human, in need thereof a therapeutically-effective amount of a compound of any of claims 1–3.

6. A method as in claim 5, wherein a disorder or disease responsive to positive modulation of the $GABA_A$ receptor complex is treated.

7. A method as in claim 5, wherein anxiety, sleep disorders, memory disorders, epilepsy or any other convulsive disorder is treated.

8. The method as in claim 5, wherein the active ingredient is administered in form of a pharmaceutical composition thereof, in which it is present together with a pharmaceutically-acceptable carrier or diluent.

* * * * *